(12) United States Patent
Chen (10) Patent No.: US 9,697,209 B2
(45) Date of Patent: Jul. 4, 2017

(54) MULTIMEDIA AUTHORING METHOD FOR ASSISTANCE IN PHYSICAL EXERCISE AND NON-VOLATILE COMPUTER-READABLE STORAGE MEDIUM

(71) Applicant: Oxygen Fitness Limited, Taipei (TW)

(72) Inventor: Yin-Chung Chen, Taipei (TW)

(73) Assignee: OXYGEN FITNESS LIMITED, Taipei (TW)

(\*) Notice: Subject to any disclaimer, the term of this patent is extended or adjusted under 35 U.S.C. 154(b) by 316 days.

(21) Appl. No.: 14/290,530

(22) Filed: May 29, 2014

(65) Prior Publication Data

US 2015/0261764 A1   Sep. 17, 2015

(30) Foreign Application Priority Data

Mar. 12, 2014   (TW) .............................. 103108772 A (51) Int. Cl.

| | |
|---|---|
| *G06F 17/00* | (2006.01) |
| *G06F 17/30* | (2006.01) |
| *G06Q 30/02* | (2012.01) |
| *A63B 24/00* | (2006.01) |
| *G06F 19/00* | (2011.01) |
| *G09B 15/00* | (2006.01) |
| *G11B 27/10* | (2006.01) |

(52) U.S. Cl.
CPC .. *G06F 17/30056* (2013.01); *G06F 17/30017* (2013.01); *A63B 24/0062* (2013.01); *A63B 24/0084* (2013.01); *G06F 17/30873* (2013.01); *G06F 19/3481* (2013.01); *G06Q 30/02* (2013.01); *G09B 15/00* (2013.01); *G11B 27/105* (2013.01)

(58) Field of Classification Search
CPC ......... G06F 17/30017; G06F 17/30873; G06F 17/30056; G06F 19/3481; A63B 24/0062; G06Q 30/02; G11B 27/105; G09B 15/00
USPC .................. 715/202–209, 255; 434/247–258
See application file for complete search history.

(56) References Cited

U.S. PATENT DOCUMENTS

2010/0205228 A1\*  8/2010  Reese ................... G06Q 30/02
                                                              707/805
2014/0087341 A1\*  3/2014  Hall ...................... G09B 5/065
                                                              434/258

(Continued)

*Primary Examiner* — Quoc A Tran
(74) *Attorney, Agent, or Firm* — Maschoff Brennan (57) ABSTRACT

The disclosure provides a multimedia authoring method for assistance in physical exercise, including the following steps. According to an exercise level command, a first number of first category parameters and a second number of second category parameters are defined to generate a category parameter sequence in which the first number of first category parameters and the second number of second category parameters are arranged randomly. First category multimedia file(s) corresponding to the first number of first category parameters and second category multimedia file(s) corresponding to the second number of second category parameters are selected from a database to establish a multimedia play list in which the first category multimedia file(s) and the second category multimedia file(s) will be sorted according to the order of the first number of first category parameters and the second number of second category parameters in the category parameter sequence.

12 Claims, 5 Drawing Sheets

(56) References Cited

U.S. PATENT DOCUMENTS

2014/0147821 A1\* 5/2014 Bernard-Paroly ....... G09B 5/06
434/247
2014/0180762 A1\* 6/2014 Gilbert .................. G06Q 30/02
705/7.29

\* cited by examiner

MULTIMEDIA AUTHORING METHOD FOR ASSISTANCE IN PHYSICAL EXERCISE AND NON-VOLATILE COMPUTER-READABLE STORAGE MEDIUM

CROSS-REFERENCE TO RELATED APPLICATIONS

This non-provisional application claims priority under 35 U.S.C. §119(a) on Patent Application No(s). 103108772 filed in Taiwan, R.O.C. on Mar. 12, 2014, the entire contents of which are hereby incorporated by reference.

TECHNICAL FIELD

The disclosure relates to a multimedia authoring method, more particularly to a multimedia authoring method which is capable for assisting in physical exercises by automatically choosing multimedia information in response to the user's setting.

BACKGROUND

Since people care about physical exercise more and more in response to them being more health conscious, the recreational sport industry, such as fitness centers (or called gyms) and fitness apparatuses have become more popular than before.

Generally, most people prefer to join fitness centers, where there are fitness apparatuses (such as exercise bikes and flywheels) and professional fitness instructors, and operate some fitness apparatuses in accordance to the exercise guidance provided by one or more fitness instructors, to ensure a better exercise effect or have some specific practice. Take a group indoor cycling class as an example. To achieve a certain exercise goal of a user in this group indoor cycling class, the fitness instructor generally chooses some music with suitable rhythm according to the capacity of the user, and then uses some suitable action prompts and the selected music to help the user to control the riding speed and time period.

However, when a user exercises under a certain situation without the real-time exercise guidance provided by a fitness instructor or would like to exercise at home, because of the lack of fitness instructors, the user can not obtain any real-time and suitable personal exercise guidance based on the personal requirements. Accordingly, the user may difficultly approach the desired exercise effect.

SUMMARY

According to one or more embodiments, the disclosure provides a multimedia authoring method for assistance in physical exercise. In one embodiment, the multimedia authoring method is applied to a device and may include the following steps: deciding the first number of first category parameters and the second number of second category parameters to be at least one according to an exercise level command; generating a category parameter sequence where the first and second category parameters are arranged randomly; from a database, selecting at least one first category multimedia file which corresponds to the at least one first category parameter, and selecting at least one second category multimedia file which corresponds to the at least one second category parameter; and establishing a multimedia play list where the at least one first category multimedia file and the at least one second category multimedia file are recorded at least and are arranged according to priorities of the first and second category parameters in the category parameter sequence.

BRIEF DESCRIPTION OF THE DRAWINGS

The present disclosure will become more fully understood from the detailed description given herein below for illustration only and thus does not limit the present disclosure, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
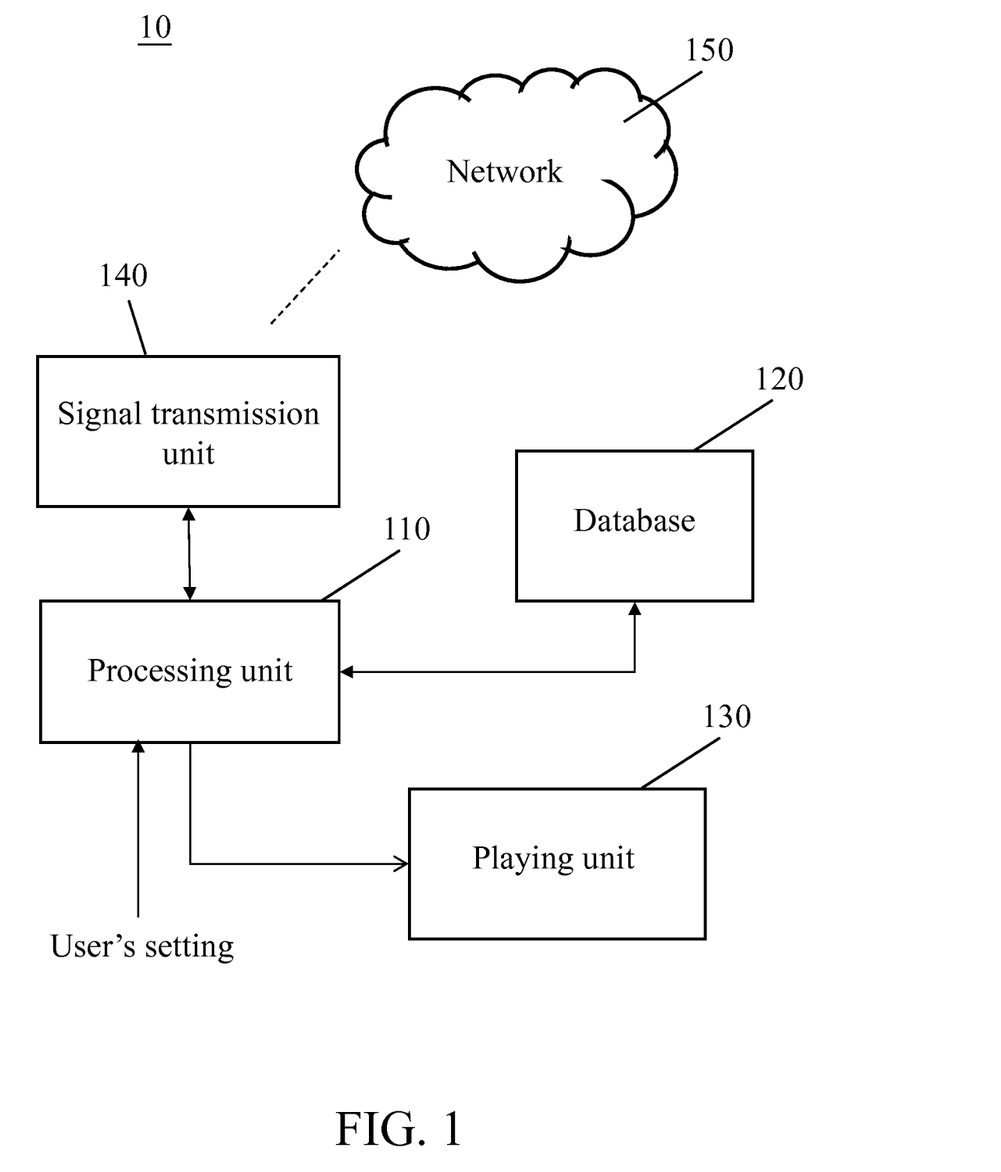
FIG. 1 is a block diagram of a device in one embodiment.

According to one or more embodiments, the disclosure provides a multimedia authoring method for assistance in physical exercise, which may be performed on a device. Referring to FIG. 1, a device 10 is shown in one embodiment. The device 10 may include a processing unit 110, a database 120, and a playing unit 130. The processing unit 110 electrically connects to the database 120 and the playing unit 130. The device 10 may be a computer, a mobile communication device, a fitness apparatus, or any possible device with computing capability and multimedia playing capability, or may be disposed on a fitness apparatus, an outdoor bicycle, or users, but the disclosure will not be limited thereto.

The processing unit 110 may execute a multimedia physical exercise assistance program stored in a storage (not shown). Based on the multimedia physical exercise assistance program, the processing unit 110 may firstly classify multimedia information inputted in the device 10 and store the classified multimedia information as multimedia options in the database 120 according to the attribute of the multimedia information. Then, based on the multimedia physical exercise assistance program, the processing unit 110 may decide suitable parameters and a suitable number thereof to select suitable multimedia options according to user's setting, to establishing a category parameter sequence where at least one part of chosen parameters are arranged randomly. After the category parameter sequence is established, in response to the multimedia physical exercise assistance program, the processing unit 110 may select some multimedia options corresponding to the chosen parameters in the category parameter sequence and record them in a multimedia play list. Finally, in response to the multimedia physical exercise assistance program, the processing unit 110 may control the playing unit 130 to play the selected multimedia options recorded in the multimedia play list.

The aforementioned attribute of multimedia information may be time length, type, speed, or any possible combination thereof, but the disclosure will not be limited thereto. The aforementioned user's setting may be an exercise level command or include an exercise level command and a time selection command. The aforementioned exercise level command may indicate the degree of difficulty of exercise guidance provided to users, and the aforementioned time selection command may indicate the time period for which users would like to exercise. Moreover, in one embodiment, the user's setting may be inputted via an input device (not shown) such as bottoms, knobs, or a display panel with touch control, but the disclosure will not be limited thereto. The aforementioned multimedia information may be video data, audio data, or both, but the disclosure will not be limited thereto. In order to clearly illustrate the disclosure, audio data is taken as an example of the multimedia information hereinafter. For example, assume one decided parameter corresponds to a certain music style and a time threshold. In this case, when the style and time length of audio data meet the music style and time threshold corresponding to the decided parameter, the processing unit 110 may select this audio data and record it in the multimedia play list for playing this audio data.

The database 120 may store multimedia information which may be real-time multimedia information, non-real-time multimedia information, default multimedia information, or any possible combination thereof. The aforementioned real-time multimedia information may be the audio data that is downloaded from a network 150 (or a cloud) in real time and then played in real time. For example, the real-time multimedia information may be audio data downloaded from a certain online music stream provided by a certain music online platform. The aforementioned non-real-time multimedia information may be audio data that can be played offline. The aforementioned default multimedia information may be the audio data that is built in the multimedia physical exercise assistance program. The database 120 may be a remote database, a database established by executing the multimedia physical exercise assistance program in the storage, or any possible combination thereof, but the disclosure will not be limited thereto.

Additionally, the device 10 may further include a signal transmission unit 140 electrically connecting to the processing unit 110. The signal transmission unit 140 may output information provided by the processing unit 110, receive multimedia information from remote terminals, transmit the received multimedia information to the processing unit 110. In one embodiment, the signal transmission unit 140 may electrically connect to an electric device (not shown) and receive multimedia information inputted by the electric device. In one embodiment, the signal transmission unit 140 may connect to a network 150 and download multimedia information from the network 150. The signal transmission unit 140 may be a cable network interface, wireless network interface, Bluetooth transmission interface, or USB transmission interface.

Figure 2:
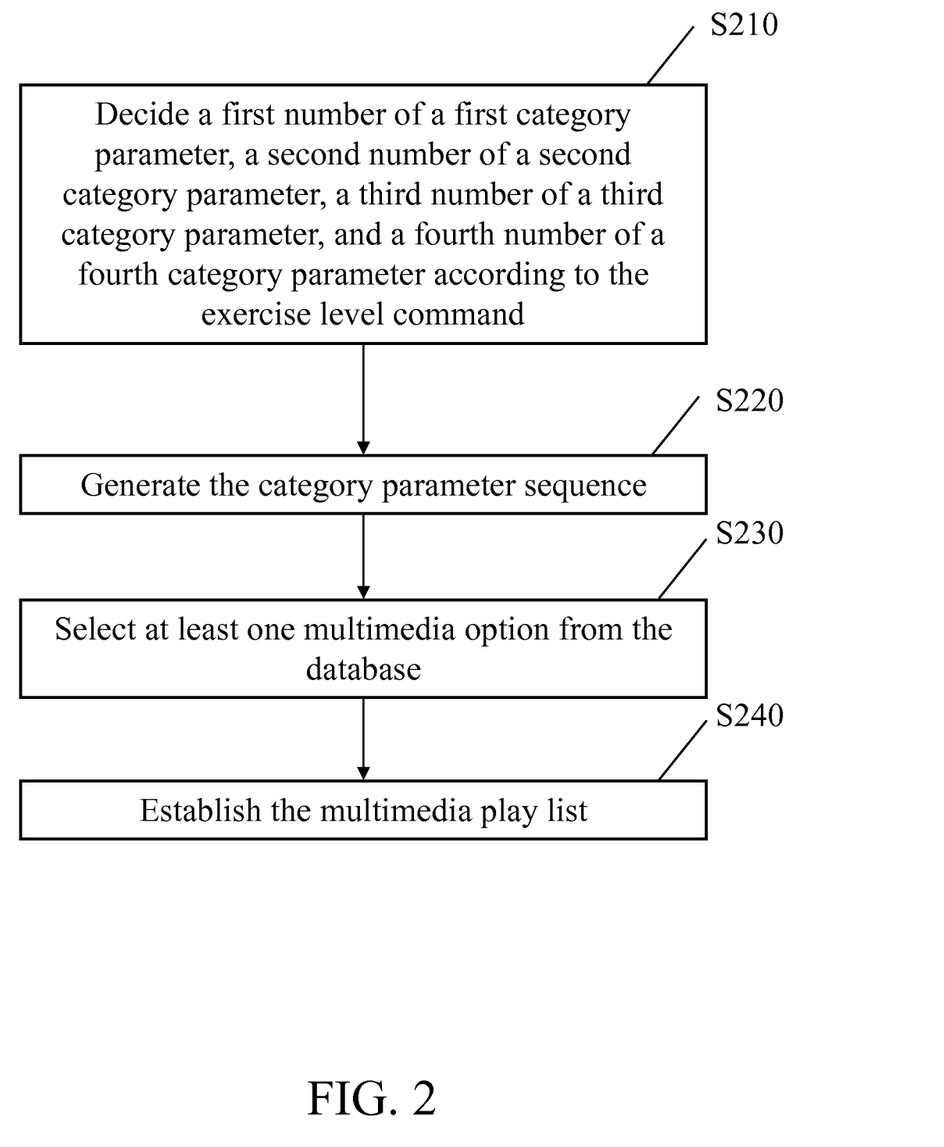
FIG. 2 is a flowchart of a multimedia authoring method for assistance in physical exercise in one embodiment.

FIG. 2 is a flowchart of a multimedia authoring method for assistance in physical exercise in one embodiment. This multimedia authoring method may be carried out with the device 10 in FIG. 1, especially with the aforementioned multimedia physical exercise assistance program executed by the processing unit 110.

As shown in step S210, a user may input the exercise level command into the processing unit 110 in the device 10 according to his or her will and requirement, whereby the processing unit 110 may decide the first number of first category parameters, the second number of second category parameters, the third number of third category parameters, and the fourth number of fourth category parameters according to the exercise level command.

In one embodiment, the aforementioned exercise level command may correspond to a total exercise grade value, the aforementioned first category parameter may correspond to a first grade value, the aforementioned second category parameter may correspond to a second grade value, the aforementioned third category parameter may correspond to a third grade value, the aforementioned fourth category parameter may correspond to a fourth grade value. In one embodiment, a sum of a product of the first grade value and the first number, a product of the second grade value and the second number, a product of the third grade value and the third number, and a product of the fourth grade value and the fourth number may be associated with the total exercise grade value. In one embodiment, the second grade value may be larger than the first grade value, the fourth grade value may be larger than the second grade value, and the third grade value may be a constant value larger than or equal to 0. Moreover, in one embodiment, the first category parameter, the second category parameter, the third category parameter, and the fourth category parameter are associated with exercise intensities. Therefore, in response to the increase of the total exercise grade value, the probability or number of times of the first category parameter, the second category parameter, the third category parameter, and the fourth category parameter appearing in the category parameter sequence may change.

In one alternate embodiment, the sum of the first number, the second number, and the fourth number may be constant or not, and the third number may be defined according to actual requirements. In order to clearly illustrate the disclosure, the following one or more embodiments are preset: the first grade value is 1; the second grade value is 2; the third grade value is 0; the fourth grade value is 3; and the sum of the product of the first grade value and the first number, the product of the second grade value and the second number, the product of the third grade value and the third number, and the product of the fourth grade value and the fourth number is equal to the total exercise grade value.

For example, assume the sum of the first number, the second number, and the fourth number is constant. In Table 1, label X represents the first category parameter, label O represents the second category parameter, label E represents the third category parameter, and label I represents the fourth category parameter. If the total exercise grade value is in a first default range (e.g. 1 to 6), the first number may decrease in response to the increase of the total exercise grade value, the second number may increase in response to the increase of the total exercise grade value, the fourth number may be 0. Herein, while the second number is larger than or equal to 1, the third number may be larger than or equal to 1. If the total exercise grade value is in a second default range (e.g. 5 to 9), the sum of the first number, the second number, and the fourth number may be equal to the total exercise grade value, the fourth number is larger than or equal to 1, the third number is larger than or equal to 1 while the second number is larger than or equal to 1; and the first default range may partially overlap the second default range.

TABLE 1

| Class # | Total exercise grade value | Permutation(s) of XOEI |
|---|---|---|
| 1 | 3 | XXX |
| 2 | 4 | XXEO, XEOX, EOXX |

TABLE 1-continued

| Class # | Total exercise grade value | Permutation(s) of XOEI |
|---|---|---|
| 3 | 5 | XEOO, EOXO, EOOX |
|   | 6 | EOOO |
| 4 | 5 | XXI, XIX, IXX |
|   | 6 | XOI, IOX, XIO, OIX, OXI, IXO |
|   | 7 | XII, IIX, IXI, OOI, OIO, IOO |
|   | 8 | OII, IOI, IIO |
|   | 9 | III |

In detail, as shown in Table 1, different total exercise grade values may indicate different classes which have different exercise schemes with different exercise intensities. The total exercise grade value 3 may indicate a first class which has the following exercise scheme with the elementary or easiest exercise intensity: the first number, the second number, and the fourth number are respectively 3, 0, and 0; and the third number may be defined according to actual requirements. The total exercise grade value 4 may indicate a second class which has the following exercise scheme with the intermediate exercise intensity: the first number, the second number, and the fourth number are respectively 2, 1, and 0; and the third number may be defined according to actual requirements. The total exercise grade value 5 may indicate a third class which has the exercise schemes with the high-intermediate exercise intensity, or indicate a fourth class which has the exercise schemes with the advanced exercise intensity. In response to the total exercise grade value 5, the third class may have the following exercise scheme: the first number, the second number, and the fourth number are respectively 1, 2, and 0, and the third number may be defined according to actual requirements. In response to the total exercise grade value 5, the fourth class may have the following exercise scheme: the first number, the second number, and the fourth number are respectively 2, 0, and 1, and the third number may be defined according to actual requirements. The total exercise grade value 6 may indicate the third class which has the exercise schemes with the high-intermediate exercise intensity, or indicate the fourth class which has the exercise schemes with the advanced exercise intensity. In response to the total exercise grade value 6, the third class may have the following exercise scheme: the first number, the second number, and the fourth number are respectively 0, 3, and 0, and the third number may be defined according to actual requirements. In response to the total exercise grade value 6, the fourth class may have the following exercise scheme: the first number, the second number, and the fourth number are respectively 1, 1, and 1, and the third number may be defined according to actual requirements. The total exercise grade value 7 may indicate the fourth class which has the following exercise scheme with the advanced exercise intensity: the first number, the second number, and the fourth number are respectively 0, 0, and 2, or are respectively 0, 2, and 1; and the third number may be defined according to actual requirements. The total exercise grade value 8 may indicate the fourth class which has the following exercise scheme with the advanced exercise intensity: the first number, the second number, and the fourth number are respectively 0, 1, and 2; and the third number may be defined according to actual requirements. The total exercise grade value 9 may indicate the fourth class which has the following exercise scheme with the advanced exercise intensity: the first number, the second number, and the fourth number are respectively 0, 0, and 3; and the third number may be defined according to actual requirements.

Moreover, when the total exercise grade value is 5 or 6, the processing unit 110 may randomly select the third class or the fourth class.

In an alternate example, assume the sum of the first number, the second number, and the fourth number is not constant, as shown in Table 2, where label X represents the first category parameter, label O represents the second category parameter, label E represents the third category parameter, and label I represents the fourth category parameter. The total exercise grade value 3 may have the following one or more exercise schemes: the first number, the second number, and the fourth number are respectively 3, 0, and 0, or are respectively 1, 1, and 0, or are respectively 0, 0, and 1, and the third number may be defined according to actual requirements. The total exercise grade value 4 may have the following one or more exercise schemes: the first number, the second number, and the fourth number are respectively 4, 0, and 0, or are respectively 2, 1, and 0, or are respectively 1, 0, and 1, or are respectively 0, 2, and 0, and the third number may be defined according to actual requirements. The one or more exercise schemes for the rest of the total exercise grade values can be deduced by analogy, and thus not repeated hereinafter.

TABLE 2

| Class # | Total exercise grade value | Permutation(s) of XOEI |
|---|---|---|
| 1 | 3 | XXX, XEO, EOX, I |
| 2 | 4 | XXXX, XXEO, XEOX, EOXX, XI, IX, EOO |

In one alternate embodiment, the aforementioned exercise level command may first indicate one intensity level and then randomly specify one of at least one total exercise grade value (or called total exercise grade value option) corresponding to the intensity level, to set one or more parameters and the number thereof. For example, as shown in Table 1, when the exercise level command may indicate the advanced exercise intensity (i.e. the fourth class), since the fourth class may correspond to five different total exercise grade values, one of the five total exercise grade values may be randomly selected, such as the total exercise grade value 7.

In the following one or more embodiments, the constant sum of the first number, the second number, and the fourth number is taken as an example to clearly illustrate the disclosure.

As shown in step S220, the processing unit 110 may combine and arrange a first number of first category parameters, a second number of second category parameters, a third number of third category parameters, and a fourth number of fourth category parameters to generate the category parameter sequence. The category parameter sequence has a sequence length which may correspond to the sum of the first number, the second number, and the fourth number but ignore the third number. In one embodiment, a first number of first category parameters, a second number of second category parameters, and a fourth number of fourth category parameters may randomly be arranged in the category parameter sequence, as shown in Table 1. For example, there is one permutation or arrangement for the category parameter sequence when the total exercise grade value is 3. For example, there are three permutations for the category parameter sequence when the total exercise grade value is 4. The disclosure does not have any limitation on the location of the third category parameter in the category parameter sequence. In one embodiment, the third category parameter may be inserted in front of one second category parameter after a first number of first category parameters, a second number of second category parameters and a third number of fourth category parameters are arranged, as shown in Table 1. For example, assume the third number is 1. In this case, the unique third category parameter may be located in front of the first one of a second number of second category parameters.

In response to the same total exercise grade value, since there may be many permutations of the first category parameter, the second category parameter, the third category parameter, and the fourth category parameter for the category parameter sequence (e.g. there are 3 permutations for the total exercise grade value 4 in Table 1), the processing unit 110 may randomly select one of the permutations (e.g. XEOX). If next time the exercise level command specifying the total exercise grade value 4 is inputted again, the processing unit 110 may randomly select another one of the permutations (e.g. XXEO) which is different from the previous selected permutation.

As shown in step S230, the processing unit 110 may, from the database 120, select at least one multimedia option corresponding to the first category parameter, the second category parameter, the third category parameter, or the fourth category parameter according to the category parameter sequence. Herein, the selected multimedia option corresponding to the first category parameter is called a first category multimedia file, the selected multimedia option corresponding to the second category parameter is called a second category multimedia file, the selected multimedia option corresponding to the third category parameter is called a third category multimedia file, and the selected multimedia option corresponding to the fourth category parameter is called a fourth category multimedia file. In one embodiment, when in the database 120 there is only one multimedia option corresponding to the first category parameter, no matter how many of the first numbers of first category parameters are, the processing unit 110 will only select this unique multimedia option as the first category multimedia file. In one embodiment, when in the database 120 there are many multimedia options corresponding to the first category parameter, the processing unit 110 may select one or more of the multimedia options, whose quantity is less than or equal to the first number, to be the one or more first category multimedia files.

In the disclosure, the database 120 may store at least one multimedia option corresponding to the first category parameter, at least one multimedia option corresponding to the second category parameter, at least one multimedia option corresponding to the third category parameter, and at least one multimedia option corresponding to the fourth category parameter. For example, when there is only one multimedia option corresponding to the first category parameter in the database 120, this multimedia option corresponding to the first category parameter may be the default multimedia information corresponding to the first category parameter. For example, when there are many multimedia options corresponding to the first category parameter in the database 120, at least one of the multimedia options corresponding to the first category parameter may be the default multimedia information corresponding to the first category parameter.

In the following one or more embodiments, the selected first category multimedia file, the selected second category multimedia file, the selected third category multimedia file, and the selected fourth category multimedia file are respectively called selected multimedia information to clearly illustrate the disclosure.

Then, as shown in step S240, the processing unit 110 may record the selected multimedia information, whose quantity corresponds to the quantity of its corresponding parameter, to establish the multimedia play list. For example, the quantity of selected first category multimedia files corresponds to the first number. The recorded one or more multimedia files in the multimedia play list may be arranged according to the order of the parameters in the category parameter sequence.

In one embodiment, if in the category parameter sequence the quantity of a certain parameter is larger than or equal to the quantity of selected multimedia information, the processing unit 110 may record at least one piece of the selected multimedia information many times in the multimedia play list until the quantity of the recorded multimedia information appearing in the multimedia play list is equal to the quantity of the corresponding parameter appearing in the category parameter sequence. For example, when there are three first category parameters in the category parameter sequence (e.g. the category parameter sequence corresponding to the total exercise grade value that is 3 as shown in Table 1), and there is only one first category multimedia file selected in step S230, this first category multimedia file may be recorded three times. For example, when there are three first category parameters in the category parameter sequence (e.g. the category parameter sequence corresponding to the total exercise grade value that is 3 as shown in Table 1), and there are only two first category multimedia files selected in step S230, the processing unit 110 may record one of the two first category multimedia files three times. For example, when there are three first category parameters in the category parameter sequence (e.g. the category parameter sequence corresponding to the total exercise grade value that is 3 as shown in Table 1), and there are three first category multimedia files selected in step S230, the processing unit 110 may directly record the three first category multimedia files.

Finally, after the multimedia play list is established, the processing unit 110 may control the playing unit 130 to sequentially play the multimedia information recorded in the multimedia play list. In one embodiment, the multimedia play list corresponds to or has a playing time length which may be specified by the time selection command provided by users, or be a default playing time length. In one embodiment, this playing time length may decide the sequence length of the category parameter sequence (i.e. the amount of all parameters in the category parameter sequence).

Figure 3:
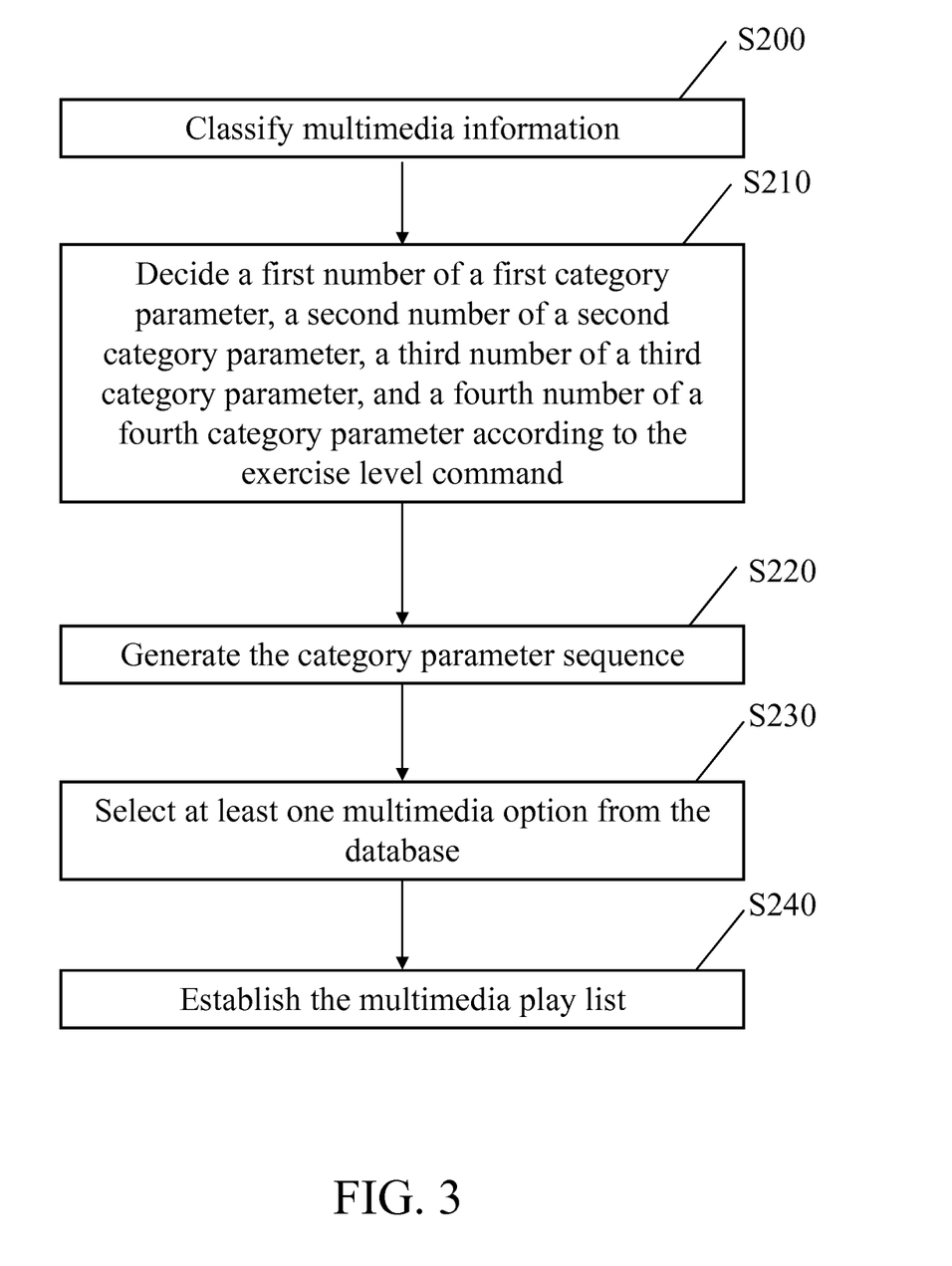
FIG. 3 is a flowchart of a multimedia authoring method for assistance in physical exercise in one embodiment.

FIG. 3 is a flowchart of a multimedia authoring method for assistance in physical exercise in one embodiment. Compared with the multimedia authoring method shown in FIG. 2, the multimedia authoring method in FIG. 3 further includes step S200.

As shown in step S200, when executing the multimedia physical exercise assistance program first or executing the multimedia physical exercise assistance program every time, the processing unit 110 may classify multimedia information in advance. In one embodiment, the processing unit 110 may automatically classify multimedia information according to at least one tag of each piece of multimedia information. The one or more tags of one piece of multimedia information may include a time tag (e.g. an end-time tag or a start-time tag), an artist tag, a title tag, a year tag, a genre tag (or a style tag), an album tag, a speed tag, a hot tag, or any possible combination thereof, but the disclosure will not be limited thereto.

Take the time tag as an example. According to the time tag of multimedia information, the processing unit 110 may determine whether to mark one piece of multimedia information as a multimedia option to be selected. Specifically, the first category parameter may correspond to a first time threshold, the second category parameter may correspond to a second time threshold, the third category parameter may correspond to a third time threshold, and the fourth category parameter may correspond to a fourth time threshold. When in the database 120 there is at least one piece of multimedia information whose time length meets (e.g. equals to) the first time threshold, the second time threshold, the third time threshold, or the fourth time threshold, this piece of multimedia information may be marked as a multimedia option corresponding to the first category parameter, the second category parameter, the third category parameter, or the fourth category parameter. For example, assume the first time threshold is 6 minutes, the second time threshold is 8 minutes, the third time threshold is 7 minutes, the fourth time threshold is 10 minutes, and there are 3 pieces of about 11 minutes of multimedia information, 1 piece of about 7 minutes of multimedia information, 7 pieces of about 6 minutes of multimedia information, 5 pieces of about 8 minutes of multimedia information, and 2 pieces of about 10 minutes of multimedia information in the database 120. In this case, the 2 pieces of about 10 minutes of multimedia information may be marked as the multimedia options corresponding to the fourth category parameter, the 1 piece of about 7 minutes of multimedia information may be marked as the multimedia option corresponding to the third category parameter, the 7 pieces of about 6 minutes of multimedia information may be marked as the multimedia options corresponding to the first category parameter, and the 5 pieces of about 8 minutes of multimedia information may be marked as the multimedia options corresponding to the third category parameter. However, the 3 pieces of about 11 minutes of multimedia information may not be marked automatically but users may be able to define them.

Take the style tag of music as an example. The processing unit 110 may determine whether one piece of multimedia information should be marked as an available multimedia option, according to the style tag of this piece of multimedia information. The aforementioned style tag may indicate Jazz, Rock, Soul, Country, Classical, R&B, House, Folk, Hip-hop, Bossa Nova, New age, Remix, Trance, Top pop, Oldies, Emotion, Lounge, or World music, but the disclosure will not be limited thereto. Specifically, the first category parameter may correspond to a first category, a second category, and a third category, the second category parameter may correspond to a fourth category, the third category parameter may correspond to a fifth category, and the fourth category parameter may correspond to a sixth category. The first category to the sixth category may correspond to one or more style tags. For example, the first category may include Top pop music, dance music, and rock music. For example, the second category may include Chinese pop music and Asia pop music. For example, the third category may include hip-hop music and R&B music. For example, the fourth category may include House music, Trance music, Remix music, or other similar music with heavy rhythm and less lyrics. For example, the fifth category may include Lounge, World, New age, Jazz music, and other similar light music with fewer lyrics. For example, the sixth category may include aggressive music, Emotion music, and Oldies music. In one embodiment, the same category in the multimedia play list may be played 2 times at most.

Figure 4:
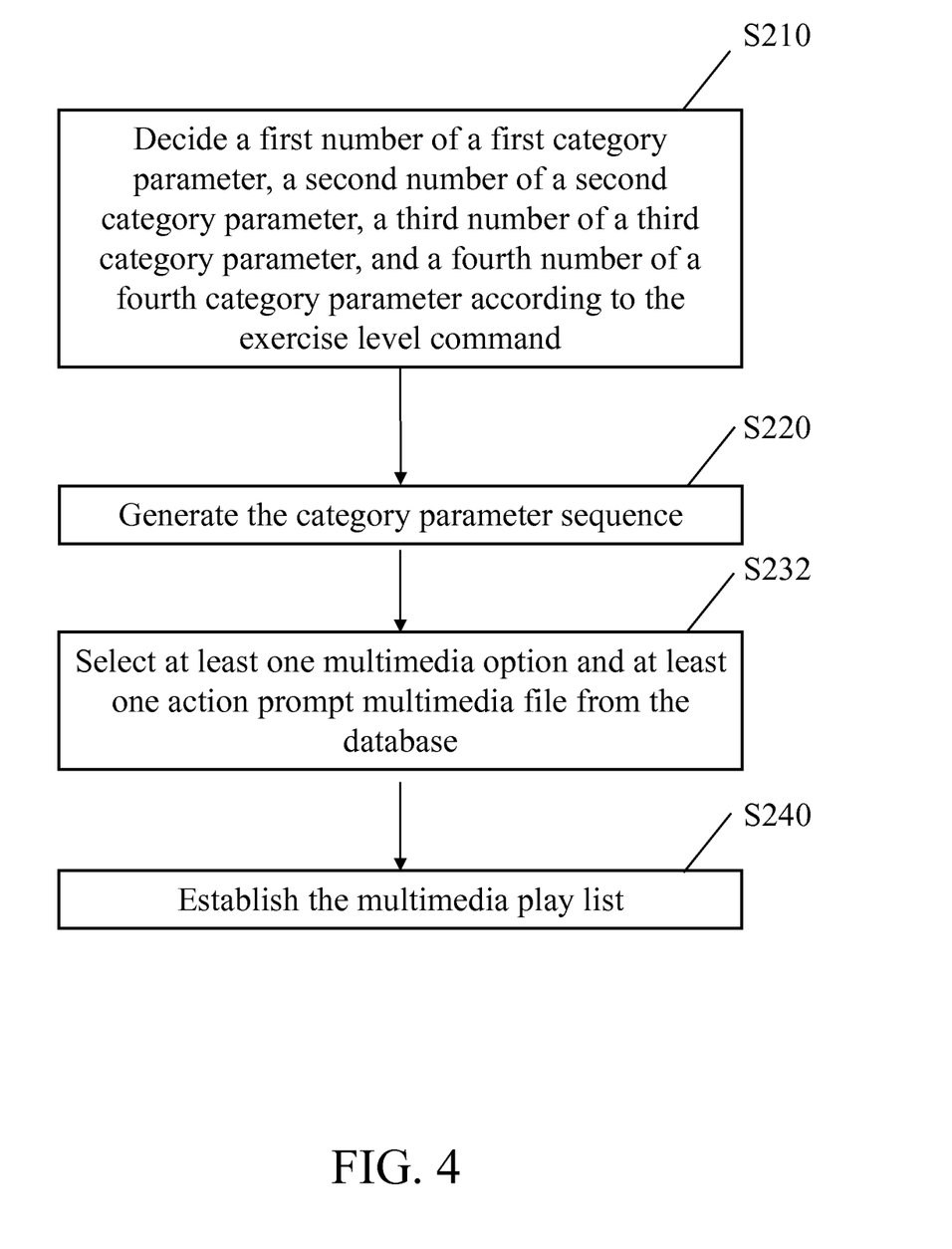
FIG. 4 is a flowchart of a multimedia authoring method for assistance in physical exercise in one embodiment.

FIG. 4 is a flowchart of a multimedia authoring method for assistance in physical exercise in one embodiment. Compared with the multimedia authoring method shown in FIG. 2, the multimedia authoring method in FIG. 4 includes step S232.

As shown in step S232, the processing unit 110 may select at least one multimedia option and at least one action prompt multimedia file from the database 120 according to the exercise level command. The at least one action prompt multimedia file may correspond to the first category multimedia file, the second category multimedia file, the third category multimedia file, or the fourth category multimedia file at least. When the playing unit 130 plays the first category multimedia file, the second category multimedia file, the third category multimedia file, or the fourth category multimedia file corresponding to the action prompt multimedia file, the playing unit 130 may also play the action prompt multimedia file. The disclosure does not have any limitation on the content, number, and time point to be started of action prompt multimedia files. In one embodiment, the playing of the action prompt multimedia file may start at a default time point on the time length of the first category multimedia file, the second category multimedia file, the third category multimedia file, or the fourth category multimedia file corresponding to the action prompt multimedia file. In one embodiment, the at least one action prompt multimedia file may be stored in the database 120 in advance.

Figure 5:
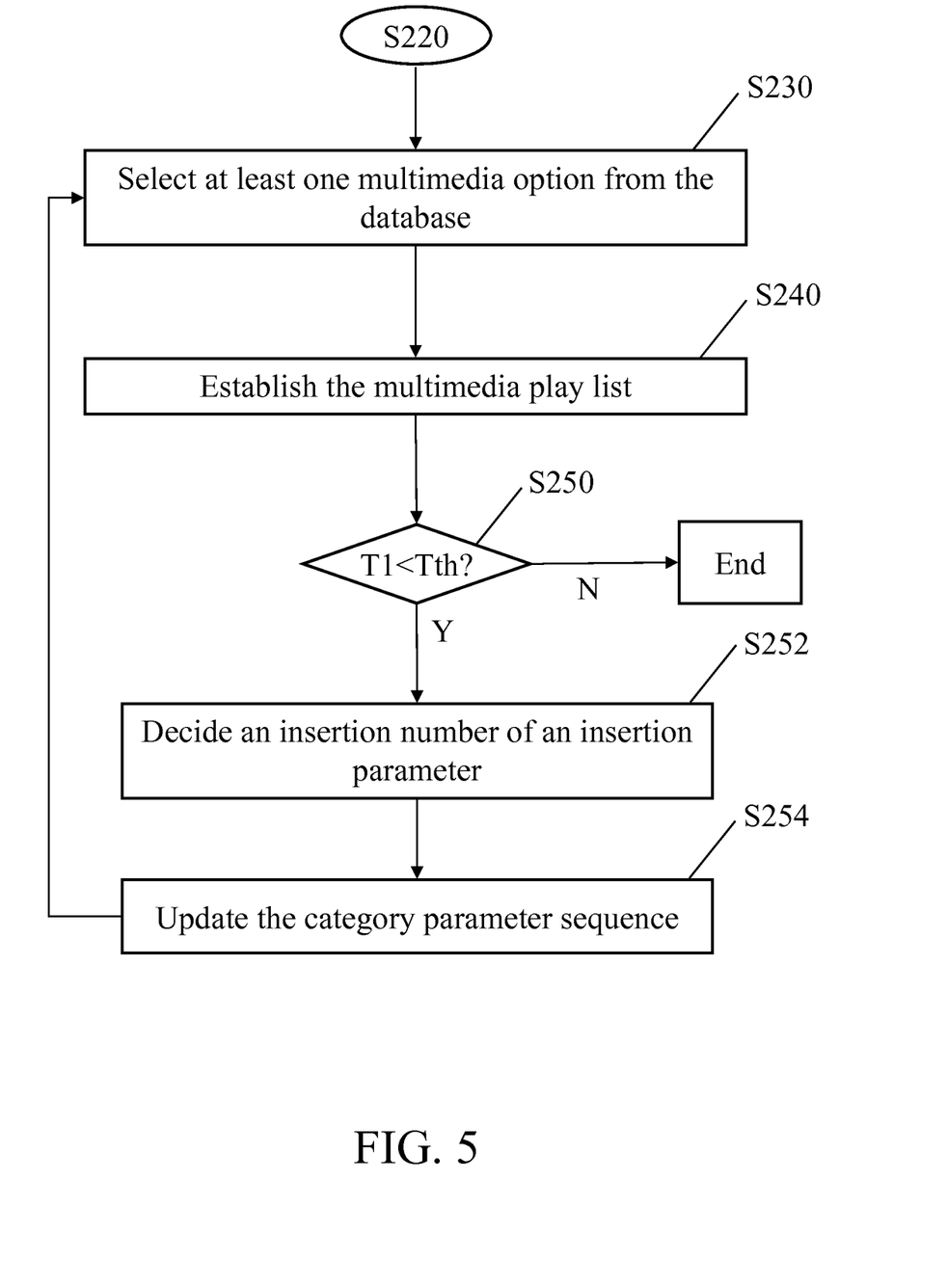
FIG. 5 is a flowchart of a multimedia authoring method for assistance in physical exercise in one embodiment.

FIG. 5 is a flowchart of a multimedia authoring method for assistance in physical exercise in one embodiment. Compared with the multimedia authoring method shown in FIG. 2, the multimedia authoring method in FIG. 5 further includes step S250 and step S252.

As shown in step S250, after the processing unit 110 has established the multimedia play list in step S240, the processing unit 110 may further determine whether the playing time length T1 related with the multimedia play list is less than a playing time threshold Tth which may be specified by the time selection command inputted by users, or be a default playing time length.

When the playing time length T1 is shorter than the playing time threshold Tth, the processing unit 110 may decide or choose the insertion number of insertion parameters to be newly added according to the difference between the playing time length T1 and the playing time threshold Tth, as shown in step S252. In one embodiment, the aforementioned insertion parameter may be the first category parameter, the second category parameter, the third category parameter, or the fourth category parameter. Hereinafter, take the first category parameter as one example of the insertion parameter to clearly illustrate the disclosure.

For example, assume the playing time length T1 related with the multimedia play list corresponding to the category parameter sequence "XXEO" is 30 minutes, and the playing time threshold Tth is 60 minutes. In this case, the difference between the playing time length T1 and the playing time threshold Tth is 30 minutes. Since the first category parameter corresponds to or has a first time threshold (e.g. 6 minutes), the processing unit 110 may decide five first category parameters (i.e. 30/6=5) as the insertion parameters according to the difference between the playing time length T1 and the playing time threshold Tth.

Then, as shown in step S254, the processing unit 110 may insert an insertion number of insertion parameters in the category parameter sequence (e.g. "XXEO") generated in step S220, to update the category parameter sequence.

In one embodiment, these insertion parameters may be located in the front, back, or both of the category parameter sequence that has not updated yet. Specifically, these insertion parameters may be located according to the location of at least one parameter in the category parameter sequence that has not updated yet.

Hereinafter, in order to illustrate the updated category parameter sequence, it is taken as an example that the location of the insertion parameter is set depending on the location of the second category parameter O. Assume there are 5 insertion parameters to be newly added to the category parameter sequence "XXEO", and the location of the second category parameter O is set to be in the last one third of the category parameter sequence. In this case, there are 3 permutations for the updated category parameter sequence, such as "XXXXXEOXX", "XXXXXXEOX", and "XXXXXXXEO". Therefore, the processing unit 110 may select one of the 3 permutations as the updated category parameter sequence.

For example, assume there are 2 insertion parameters to be newly added to the category parameter sequence "XEOX", and the location of the second category parameter O is set to be in the second one third of the category parameter sequence. In this case, there are 2 permutations for the updated category parameter sequence, such as "XEOXXX" and "XXEOXX". Therefore, the processing unit 110 may select one of the 2 permutations as the updated category parameter sequence.

For example, assume there are 5 insertion parameters to be newly added to the category parameter sequence "EOOX", and the first one of the second category parameters O is set to be in the first one third of the category parameter sequence, and the location of the second one of the second category parameters "0" is set to be in the second one third of the category parameter sequence. In this case, there are 6 permutations for the updated category parameter sequence, such as "EOXOXXXXX", "EOXXOXXXX", "EOXXXOXXX", "XEOOXXXXX", "XEOXOXXXX", and "XEOXXOXXX". Therefore, the processing unit 110 may select one of the 6 permutations as the updated category parameter sequence.

For example, assume 2 insertion parameters are added to the category parameter sequence "EOOO", which has not updated, according to the locations of the 3 second category parameters O. Moreover, the first one of the 3 second category parameters O has to be located in the first one third of the category parameter sequence, the second one of the 3 second category parameters O has to be located in the second one third of the category parameter sequence, and the third one of the 3 second category parameters O has to be located in the last one third of the category parameter sequence. In this case, there are 4 permutations for the updated category parameter sequence, such as "EOOXOX", "EOOXXO", "EOXOOX", and "EOXOXO". Therefore, the processing unit 110 may select one of the 4 permutations as the updated category parameter sequence.

Hereinafter, in order to illustrate the updated category parameter sequence, it is taken as an example that the location of the insertion parameter is set depending on the locations of the second category parameter O and the fourth category parameter I.

For example, assume there are 3 insertion parameters to be added to the category parameter sequence "XEOI", the location of the second category parameter O is set to be located in the second one third of the category parameter sequence, and the fourth category parameter I is set to be located in the last one third of the category parameter sequence. In this case, there are 6 permutations for the updated category parameter sequence, such as "XEOXXIX", "XEOXXXI", "XXEOXIX", "XXEOXXI", "XXXEOIX", and "XXXEOXI". Therefore, the processing unit 110 may select one of the 6 permutations as the updated category parameter sequence.

For example, assume there are 6 insertion parameters to be newly added to the category parameter sequence "EOIO", the first one of the second category parameters O is set to be located in the first one third of the category parameter sequence, the second one of the second category parameters O is set to be located in the last one third of the category parameter sequence, and the fourth category parameter I is set to be located in the second one third of the category parameter sequence. In this case, there are 24 permutations for the updated category parameter sequence, such as "EOXIXXXOXX", "EOXIXXXXOX", "EOXIXXXXXO", "EOXXIXXOXX", "EOXXIXXXOX", "EOXXIXXXXO", "EOXXXIXOXX", "EOXXXIXXOX", "EOXXXIXXXO", "EOXXXXIOXX" "EOXXXXIXOX", "EOXXXXIXXO", "XEOIXXXOXX", "XEOIXXXXOX", "XEOIXXXXXO", "XEOXIXXOXX", "XEOXIXXXOX", "XEOXIXXXXO", "XEOXXIXOXX", "XEOXXIXXOX", "XEOXXIXXXO", "XEOXXXIOXX", "XEOXXXIXOX", and "XEOXXXIXXO". Therefore, the processing unit 110 may select one of the 24 permutations as the updated category parameter sequence.

In one alternate embodiment, the insertion parameters may randomly be located in the front, back, or both of the category parameter sequence that has not been updated. For example, the insertion parameter may be located in front of the category parameter sequence "XXEO" that has not been updated, so that the updated category parameter sequence may become "XXXXXXXEO".

Then, as shown in step S230, the processing unit 110 may select at least one multimedia option from the database 120 according to the updated category parameter sequence. Specifically, the processing unit 110 may select at least one multimedia option corresponding to the one or more insertion parameters in the updated category parameter sequence. In other words, the processing unit 110 may select at least one first category multimedia file (or called insertion multimedia file) corresponding to the one or more newly-added first category parameters. The detailed operation about the selection of the at least one multimedia option can be referred to the relative description in FIG. 2, and thus is not repeated hereinafter.

Finally, as shown in step S240, the processing unit 110 may further record the above selected multimedia information (i.e. the one or more insertion multimedia files), to establish a new multimedia play list, i.e. to update the multimedia play list that has not been updated. Specifically, the processing unit 110 may make the number of recorded multimedia information correspond to the number of parameters corresponding to the recorded multimedia information, and may also arrange the recorded multimedia information according to the one or more parameters, corresponding to the recorded multimedia information, in the updated category parameter sequence. The detailed operation about the recording of the selected multimedia information can be referred to the relative description in FIG. 2, and thus will not be repeated hereinafter.

As set forth above, the disclosure may decide the kind and number of required parameters according to the user's setting and may randomly arrange at least one part of the decided parameters to establish a category parameter sequence. Then, suitable multimedia information may be selected according to the parameters in the category parameter sequence automatically, be sorted and recorded according to the order of the parameters in the category parameter sequence, and be eventually played sequentially. Therefore, users may start, stop, speed up, or speed down the physical activities according to the content, e.g. rhythms, of played multimedia information.

Moreover, the disclosure may also select one ore more suitable action prompt multimedia files according to one or more decided parameters so that when multimedia information corresponding to one or more decided parameters is being played, the one or more selected action prompt multimedia files may be played to provide users with more real-time personal exercise guidance.

Accordingly, even though a user exercises under a certain situation without the real-time exercise guidance provided by a fitness instructor or would like to exercise at home, the user can obtain the personal exercise guidance provided by the disclosure, thereby approach the desired fitness effect.

What is claimed is:

1. A multimedia authoring method for assistance in physical exercise, the multimedia authoring method applied to a device and comprising:
    deciding the first number of first category parameters and the second number of second category parameters to be at least one according to an exercise level command;
    generating a category parameter sequence where the at least one first category parameter and the at least one second category parameter are arranged randomly;
    from a database, selecting at least one first category multimedia file which corresponds to the at least one first category parameter, and selecting at least one second category multimedia file which corresponds to the at least one second category parameter; and
    wherein arranging randomly by select the first category multimedia file and the second category multimedia file is performed according to tags of the first category multimedia file and the second category multimedia file; and
    wherein the first category parameter corresponds to a first time threshold, the second category parameter corresponds to a second time threshold, and when in the database there is a piece of multimedia information whose time length meets the first time threshold or the second time threshold, the piece of multimedia information is marked as an available multimedia option;
    establishing a multimedia play list where the at least one first category multimedia file and the at least one second category multimedia file are recorded at least and are arranged according to priorities of the first and second category parameters in the category parameter sequence,
    wherein the exercise level command corresponds to a total exercise grade value, the first category parameter corresponds to a first grade value, the second category parameter corresponds to a second grade value, a sum of a product of the first grade value and the first number and a product of the second grade value and the second number is associated with the total exercise grade value.

2. The multimedia authoring method according to claim 1, wherein the second grade value is larger than the first grade value.

3. The multimedia authoring method according to claim 2, wherein the exercise level command corresponds to one of levels of exercise intensity which corresponds to at least one total exercise grade value option, and the total exercise grade value is randomly selected from the at least one total exercise grade value option.

4. The multimedia authoring method according to claim 2, further comprising:
    deciding the third number of third category parameters to be at least one according to the exercise level command, wherein the third category parameter is boated in front of one second category parameter and corresponds to a third grade value, and a sum of the product of the first grade value and the first number, the product of the second grade value and the second number, and a product of the third grade value and the third number is associated with the total exercise grade value;
    selecting at least one third category multimedia file corresponding to the at least one third category parameter in the database; and
    recording the third category multimedia file in the multimedia play list where the at least one first category multimedia file, the at least one second category multimedia file, and the at least one third category multimedia file are arranged according to priorities of the first, second and third category parameters in the category parameter sequence.

5. The multimedia authoring method according to claim 4, further comprising:
    from the database, selecting at least one action prompt multimedia the which corresponds to the first category multimedia file, the second category multimedia file, or the third category multimedia file at least; and
    playing the action prompt multimedia file when the first category multimedia file, the second category multimedia file, or the third category multimedia file corresponding to the action prompt multimedia file is played.

6. The multimedia authoring method according to claim 4, wherein a length of the category parameter sequence is constant, and when the total exercise grade value increases and is in a first default range, the first number decreases and the second number increases.

7. The multimedia authoring method according to claim 6, wherein when the total exercise grade value is in a second default range, the multimedia authoring method further comprises:
    deciding the fourth number of fourth category parameters to be at least one according to the exercise level command so that the category parameter sequence further comprises the at least one fourth category parameter and the first, second and fourth category parameters are arranged in the category parameter sequence randomly; and selecting at least one fourth category multimedia file, which corresponds to the at least one fourth category parameters, from the database; and
    recording the at least one selected fourth category multimedia file in the multimedia play list where the at least one first category multimedia file, the at least one second category multimedia file, the at least one third category multimedia file, and
    the at least one fourth category multimedia file are arranged according to priorities of the first, second, third and fourth category parameters in the category parameter sequence, wherein the fourth category parameter corresponds to a fourth grade value;
    the fourth grade value is larger than the second grade value;

a sum of the product of the first grade value and the first number, the product of the second grade value and the second number, the product of the third grade value and the third number, and a product of the fourth grade value and the fourth number is equal to the total exercise grade value; and the first default range partially overlaps the second default range.

8. The multimedia authoring method according to claim 1, wherein a playing time length of the multimedia play list is specified by a time selection command or is a first default playing time length.

9. The multimedia authoring method according to claim 8, wherein after the multimedia play list is established, the multimedia authoring method further comprises:

determining whether the playing time length of the multimedia play list is shorter than a playing time threshold which is specified by the time selection command or is a second default playing time length;

deciding the insertion number of insertion parameters to be at least one according to a difference between the playing time length of the multimedia play list and the playing time threshold so that the updated category parameter sequence further comprises the at least one insertion parameter when the playing time length of the multimedia play list is shorter than the playing time threshold;

selecting at least one insertion multimedia file, which corresponds to the at least one insertion parameter, from the database; and updating the multimedia play list by recording the at least one insertion multimedia file so that in the updated multimedia play list the at least one insertion multimedia file is arranged according to priority of the at least one insertion parameter in the updated category parameter sequence.

10. The multimedia authoring method according to claim 9, wherein the at least one insertion parameter is randomly and respectively inserted in the front, back, or both of the category parameter sequence before updating.

11. The multimedia authoring method according to claim 9, wherein according to a location of at least one parameter in the category parameter sequence before updating, the at least one insertion parameter is respectively located in the front, back, or both of the category parameter sequence before updating.

12. A non-transitory computer-readable storage medium storing a multimedia physical exercise assistance program comprising executable instructions that, when executed, perform the multimedia authoring method of claim 1.

* * * * *